United States Patent
Al-Anzi

(10) Patent No.: US 10,045,880 B2
(45) Date of Patent: Aug. 14, 2018

(54) COOLING SYSTEM FOR PATIENTS WITH FEVER

(71) Applicant: KUWAIT UNIVERSITY, Safat (KW)

(72) Inventor: Bader Shafaqa Al-Anzi, Safat (KW)

(73) Assignee: KUWAIT UNIVERSITY, Safat (KW)

( * ) Notice: Subject to any disclaimer, the term of this patent is extended or adjusted under 35 U.S.C. 154(b) by 157 days.

(21) Appl. No.: 15/003,739

(22) Filed: Jan. 21, 2016

(65) Prior Publication Data

US 2017/0209303 A1    Jul. 27, 2017

(51) Int. Cl.
| | |
|---|---|
| *A61F 7/02* | (2006.01) |
| *A61F 7/00* | (2006.01) |
| *A61B 5/01* | (2006.01) |
| *A61B 5/00* | (2006.01) |

(52) U.S. Cl.
CPC .................. *A61F 7/02* (2013.01); *A61B 5/01* (2013.01); *A61B 5/4836* (2013.01); *A61B 5/746* (2013.01); *A61F 7/0085* (2013.01); *A61F 2007/0007* (2013.01); *A61F 2007/0056* (2013.01); *A61F 2007/0086* (2013.01); *A61F 2007/0096* (2013.01)

(58) Field of Classification Search
CPC ...... A61F 2007/0056; A61F 2007/0086; A61F 2007/0288; A61F 2007/0295; A61F 7/0085; A61F 7/0241; F23N 2035/20; G05D 23/1353
USPC ....................................................... 607/104
See application file for complete search history.

(56) References Cited

U.S. PATENT DOCUMENTS

| | | | |
|---|---|---|---|
| 2,726,658 A | 12/1955 | Chessey | |
| 4,026,299 A | 5/1977 | Sauder | |
| 4,170,998 A | 10/1979 | Sauder | |
| 2004/0059400 A1 | 3/2004 | Lin | |
| 2013/0328063 A1 | 12/2013 | Yamazaki | |
| 2014/0222121 A1* | 8/2014 | Spence | A41D 13/005 607/104 |

FOREIGN PATENT DOCUMENTS

| | | |
|---|---|---|
| JP | 2006-102450 | 4/2006 |
| JP | 2009-189757 | 8/2009 |

* cited by examiner

*Primary Examiner* — Joseph Stoklosa
*Assistant Examiner* — Tigist Demie
(74) *Attorney, Agent, or Firm* — Richard C. Litman

(57) ABSTRACT

The cooling system for patients with fever is a mechanical, fluid-based system for cooling patients suffering from fever. The cooling system for patients with fever includes a reservoir for containing a cooling fluid, which is maintained at a desired temperature. A temperature sensor is received in the reservoir. The temperature sensor is immersed in the cooling fluid for measuring the temperature thereof. A chiller is also received in the reservoir for selectively cooling the cooling fluid when the temperature thereof, measured by the temperature sensor, is above a pre-set temperature threshold. The reservoir communicates with a cooling pad, which is formed from a padded layer having at least one channel embedded therein. At least one pump and tubing is provided for circulating the cooling fluid through the reservoir and the cooling pad. In use, the cooling pad is applied to the skin of a patient with a fever.

2 Claims, 4 Drawing Sheets

COOLING SYSTEM FOR PATIENTS WITH FEVER

BACKGROUND OF THE INVENTION

1. Field of the Invention

The present invention relates to fever reduction, and particularly to a cooling system for patients with fever which operates via fluid-based thermal transfer.

2. Description of the Related Art

Fever, also known as pyrexia and febrile response, is most accurately characterized as a temporary elevation in the body's thermoregulatory set-point, causing typical body temperature to rise. A body temperature at or above 37.5° C. is typically indicative of a fever. The increase in thermoregulatory set-point triggers increased muscle contraction and causes a feeling of cold in the patient despite an increased body temperature. This results in greater heat production and efforts to conserve heat. When the set-point temperature returns to normal, a person feels hot, becomes flushed, and may begin to sweat.

Non-medicinal treatments for fever include placing a cool, damp cloth on the forehead and taking a lukewarm bath. Additionally, medications, such as ibuprofen or paracetamol, may be effective at lowering the temperature.

With regard to the non-medicinal treatments, the temperature of a cooling cloth is difficult to regulate and requires the water to be constantly changed. The same issues relate to the bath. With regard to medicinal treatments, overuse of analgesics such as ibuprofen have been shown to potentially lead to nausea, dyspepsia, gastrointestinal ulceration/bleeding, raised liver enzymes, diarrhea, constipation, nosebleed, headache, dizziness, rash, salt and fluid retention, and hypertension. Thus, a cooling system for patients with fever solving the aforementioned problems is desired.

SUMMARY OF THE INVENTION

The cooling system for patients with fever is a mechanical, fluid-based system for cooling patients suffering from fever. The cooling system for patients with fever includes a reservoir for containing a cooling fluid, which is maintained at a desired temperature. A temperature sensor is disposed in the reservoir, such that the temperature sensor is immersed in the cooling fluid for measuring the temperature thereof. A chiller is also received in the reservoir for selectively cooling the cooling fluid when the temperature thereof, measured by the temperature sensor, is above a pre-set temperature threshold.

The reservoir communicates with a cooling pad, which is formed from a padded layer having at least one channel embedded therein. A first end of an inflow tube is in fluid communication with the reservoir, and a second end thereof is in fluid communication with a first end of the at least one channel, such that the cooling fluid selectively passes from the reservoir, through the inflow tube, and into the at least one channel. A first end of an outflow tube is in fluid communication with the reservoir, and a second end thereof is in fluid communication with a second end of the at least one channel, such that the cooling fluid passes through the at least one channel, into the outflow tube, and back into the reservoir. At least one pump is provided for selectively circulating the cooling fluid through the reservoir, the inflow tube, the cooling pad and the outflow tube. In use, the cooling pad is applied to the skin of a patient with a fever, such as by making contact with the patient's forehead, for example.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
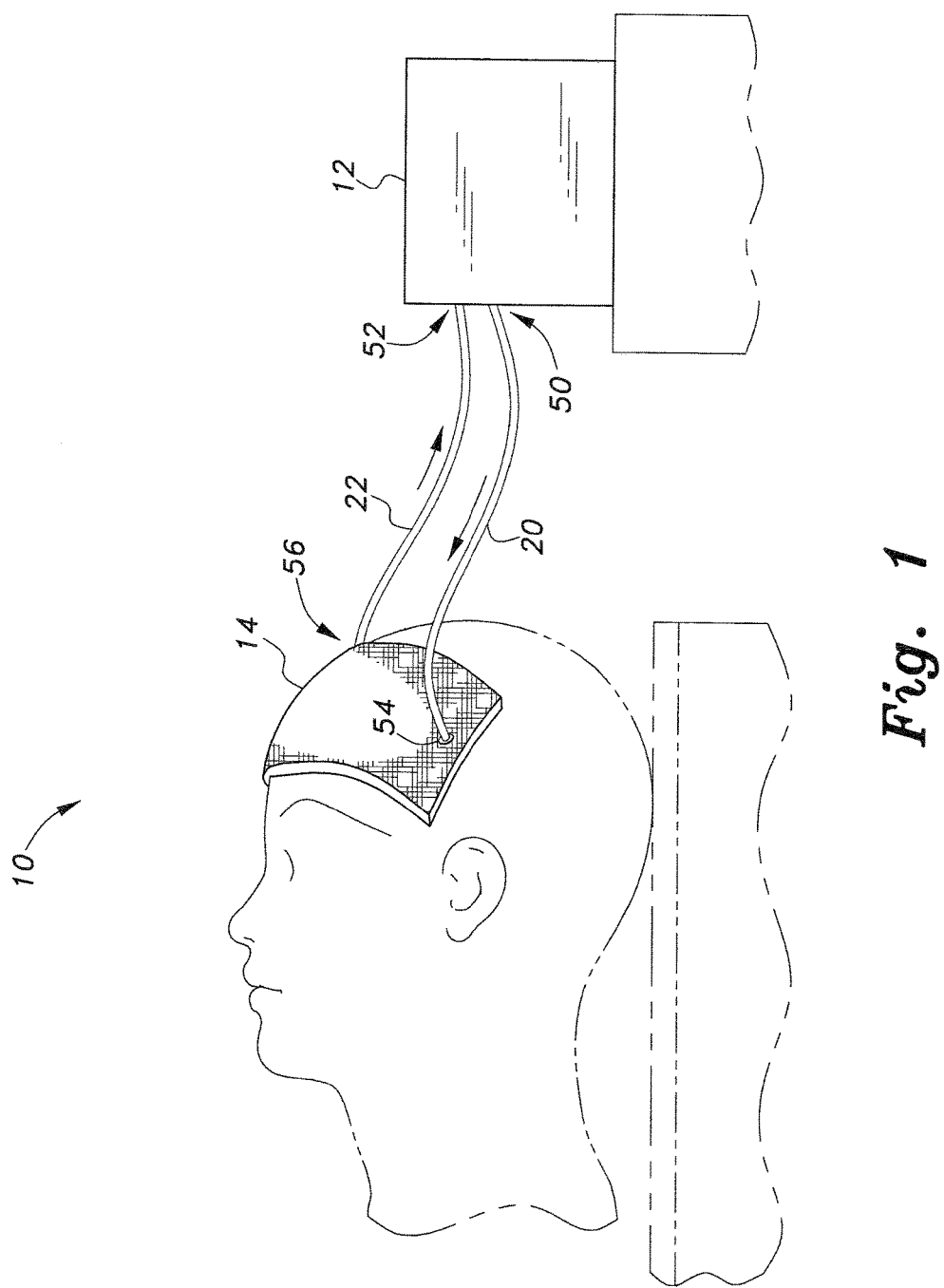
FIG. 1 diagrammatically illustrates a cooling system for patients with fever according to the present invention.
Figure 3:
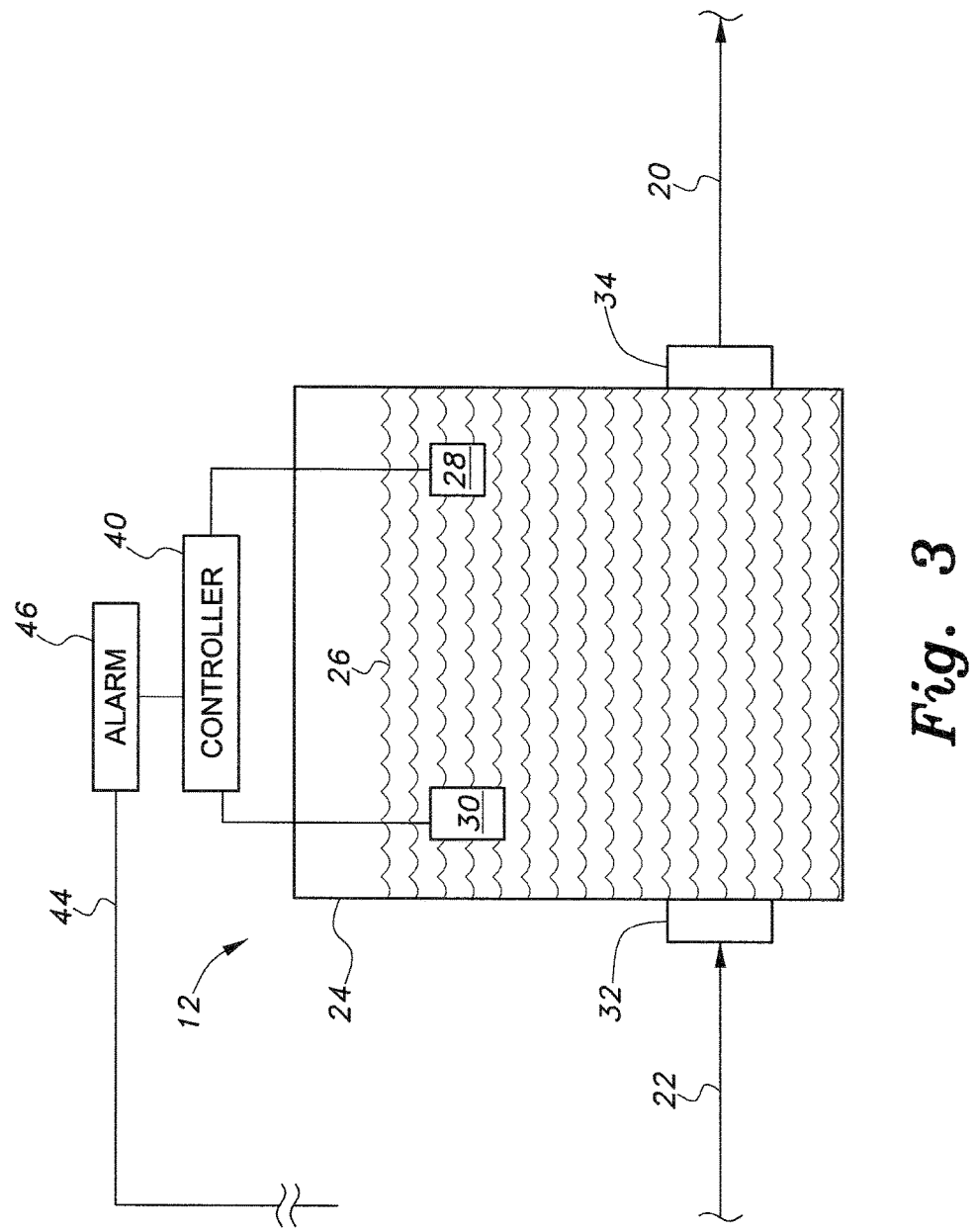
FIG. 3 schematically illustrates a cooling unit of the cooling system for patients with fever.

The cooling system for patients with fever 10 is a mechanical, fluid-based system for cooling patients suffering from fever. As shown in FIG. 1, the cooling system for patients with fever 10 includes a cooling unit 12 and a cooling pad 14. The cooling pad 14 is applied to the skin of a patient suffering from fever, such as by application to the forehead of the patient, for example, for cooling the patient via thermal transfer between the cooling unit 12 and the cooling pad 14. As shown in FIG. 3, the cooling unit 12 includes a reservoir 24 for containing a cooling fluid 26, which is maintained at a desired temperature. It should be understood that any suitable type of cooling fluid 26 may be used, such as liquid coolants, liquid water or the like.

A temperature sensor 28 is received in the reservoir 24, such that the temperature sensor 28 is immersed in the cooling fluid 26 for measuring the temperature thereof. It should be understood that the temperature sensor 28 may be a thermometer, a thermocouple, or any other suitable type of temperature sensor, as is well known in the art. A chiller 30 is also received in the reservoir 24 for selectively cooling the cooling fluid 26 when the temperature thereof, measured by the temperature sensor 28, is above a pre-set temperature threshold. It should be understood that chiller 30 may be any suitable type of chiller, cooler, refrigerator, cooling coil or the like which is suitable for cooling the cooling fluid 26 to the desired pre-set temperature. Preferably, as shown, chiller 30 is in communication with temperature sensor 28 through a controller 40, which may be any suitable type of control circuitry, computer processor or the like, which actuates the chiller 30 when the temperature measured by temperature sensor 28 is above the pre-set temperature threshold.

Figure 2:
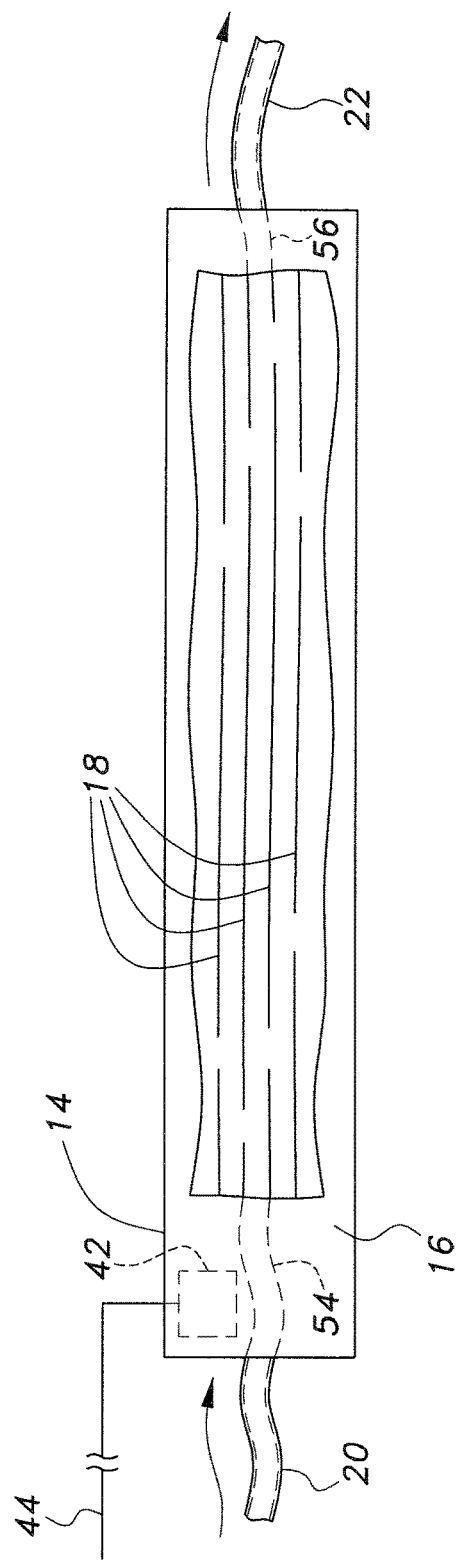
FIG. 2 is a partially cut-away plan view of a cooling pad of the cooling system for patients with fever.

The reservoir 24 communicates with the cooling pad 14, which, as best shown in FIG. 2, is formed from a padded layer 14 having at least one channel 18 embedded therein. In FIG. 2, four such channels 18 are illustrated, however it should be understood that this is shown for exemplary purposes only. Any desired number of channels 18 may be embedded within padded layer 16. It should be further understood that padded layer 16 may be formed from any suitable material which is comfortable for application to the patient's skin and also allows for effective thermal transfer therethrough. Further, it should be understood that channels 18 may be any suitable type of passages, channels, tubes, pipes or the like, allowing the cooling fluid 26 to pass therethrough, without leakage or corrosion, and providing for effective thermal transfer from the patient's skin to the cooling fluid 26.

A first end 50 of an inflow tube 20 is in fluid communication with the reservoir 24, and a second end 54 of the inflow tube 20 is in fluid communication with a first end of the at least one channel 18. In operation, the cooling fluid 26 selectively passes from the reservoir 24, through the inflow tube 20, and into the at least one channel 18. A first end 52 of an outflow tube 22 is in fluid communication with the reservoir 24, and a second end 56 of the outflow tube 22 is in fluid communication with a second end of the at least one channel 18, such that the cooling fluid 26 passes through the at least one channel 18, into the outflow tube 22, and back into the reservoir 24.

At least one pump is provided for selectively circulating the cooling fluid 26 through the reservoir 24, the inflow tube 20, the cooling pad 14 and the outflow tube 22. In FIG. 3, pump 32 is shown being in fluid communication with outflow tube 22, and pump 34 is shown being in fluid communication with inflow tube 20. It should be understood that a single pump may alternatively be utilized for effecting circulation of the cooling fluid 26. In use, the cooling pad 14 is applied to the skin of a patient with a fever, such as by making contact with the patient's forehead, for example.

Additionally, as shown in FIG. 2, a pad temperature sensor 42 may be embedded in cooling pad 14 for directly measuring the patient's skin temperature. It should be understood that pad temperature sensor 42 may be a thermometer, a thermocouple, or any other suitable type of temperature sensor, as is well known in the art. As shown in FIGS. 2 and 3, temperature sensor 42 may be in communication with controller 40 via line 44, which may be wired or wireless, for display of the patient's temperature or for actuation of an optional alarm 46 if the patient's temperature exceeds a pre-set threshold. It should be understood that alarm 46 may be any suitable type of alarm, such as a conventional display, an auditory alarm, any suitable type of visual alarm or the like.

Figure 4:
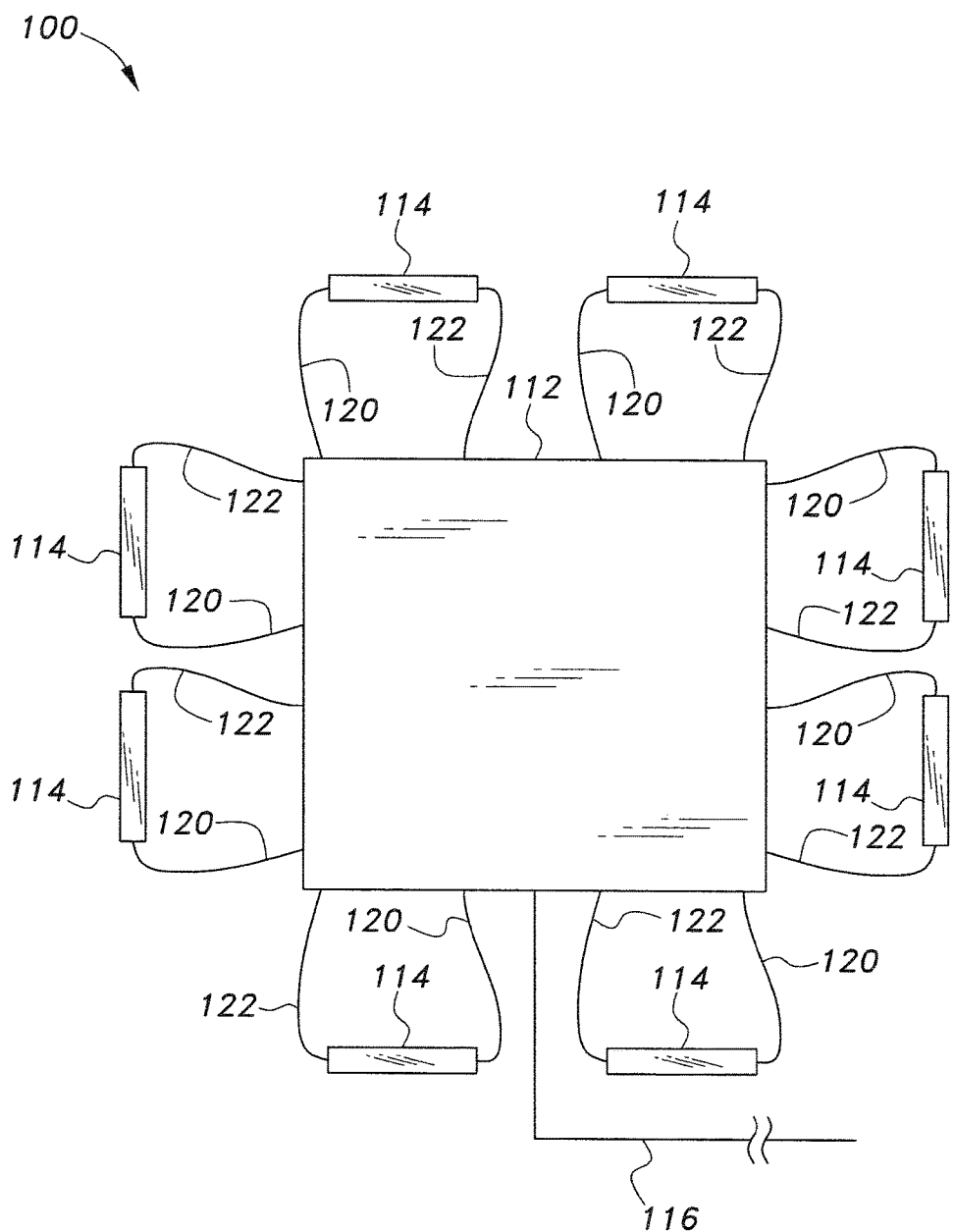
FIG. 4 diagrammatically illustrates an alternative embodiment of the cooling system for patients with fever.

In the alternative embodiment of FIG. 4, a cooling system for patients with fever 100 is adapted for use by multiple patients. The system 100 includes a plurality of cooling pads 114, which are similar to cooling pad 14 described above, along with corresponding inflow tubes and outflow tubes 120, 122 for each cooling pad 114. Each of the cooling pads 114 is in fluid communication with a central reservoir 112, similar to reservoir 12 described above, such that the cooling system for patients with fever 100 may be used by multiple patients simultaneously, with a central reservoir 112 of cooling fluid and under centralized control. Temperature and operation control may take place at the system 100, as with system 10, or may alternatively take place in an external control room, with remote communication provided by line 116, as shown. The circulation of the cooling fluid from reservoir 112 through each cooling pad 114 takes place as described above with respect to system 10, only with each cooling pad 114 selectively circulating the cooling fluid with the single, central reservoir 112.

It is to be understood that the present invention is not limited to the embodiments described above, but encompasses any and all embodiments within the scope of the following claims.

I claim:

1. A cooling system for patients with fever, consisting of:
   a reservoir for containing a cooling fluid;
   a temperature sensor received in said reservoir, such that said temperature sensor is immersed in the cooling fluid for measuring a temperature thereof;
   a chiller received in said reservoir for selectively cooling the cooling fluid when the temperature thereof, measured by said temperature sensor, is above a pre-set temperature threshold;
   a single cooling pad comprising a padded layer having at least one channel embedded therein, wherein said at least one channel has opposed first and second ends;
   an inflow tube having opposed first and second ends, the first end of the inflow tube thereof being in fluid communication with said reservoir and the second end of the inflow tube thereof being in fluid communication with the first end of the at least one channel, such that the cooling fluid selectively passes from said reservoir, through said inflow tube, and into the at least one channel;
   an outflow tube having opposed first and second ends, the first end of the outflow tube thereof being in fluid communication with said reservoir and the second end of the outflow tube thereof being in fluid communication with the second end of the at least one channel, such that the cooling fluid passes through the at least one channel, into said outflow tube, and back into said reservoir;
   a pair of pumps for selectively circulating the cooling fluid through the reservoir, the inflow tube, the cooling pad and the outflow tube, whereby the cooling pad may be applied to the skin of a patient with a fever, wherein the pair of pumps consist of an inlet pump in fluid communication with the inflow tube and an outlet pump in fluid communication with the outflow tube;
   a pad temperature sensor embedded in said cooling pad for measuring a skin temperature of the patient; and
   an alarm in communication with the pad temperature sensor such that the alarm is actuated when the skin temperature of the patient exceeds a pre-set temperature threshold.

2. The cooling system for patients with fever as recited in claim 1, wherein the at least one channel comprises a plurality of channels.

* * * * *